United States Patent [19]

Skiba et al.

[11] Patent Number: 5,718,905
[45] Date of Patent: Feb. 17, 1998

[54] PREPARATION AND USE OF NOVEL CYCLODEXTRIN-BASED DISPERSIBLE COLLOIDAL SYSTEMS IN THE FORM OF NANOSPHERES

[75] Inventors: Mohamed Skiba, Verrieres-Le-Buisson; Denis Wouessidjewe, Antony; Antony Coleman, Briis-Sous-Forges; Hatem Fessi, Paris; Jean-Philippe Devissaguet, Neuillyls; Dominique Duchene, Paris; Francis Puisieux, Maisons-Alfort, all of France

[73] Assignee: Centre National de la Recherche Scientifique (C.N.R.S.), Paris, France

[21] Appl. No.: 356,167
[22] PCT Filed: Jun. 16, 1993
[86] PCT No.: PCT/FR93/00594
§ 371 Date: Mar. 8, 1995
§ 102(e) Date: Mar. 8, 1995
[87] PCT Pub. No.: WO93/25195
PCT Pub. Date: Dec. 23, 1993

[30] Foreign Application Priority Data

Jun. 16, 1992 [FR] France .................................. 92 07 287

[51] Int. Cl.$^6$ ........................................................ A61K 9/51
[52] U.S. Cl. .......................... 424/499; 424/401; 428/402; 428/402.24; 264/4.1; 264/4.6
[58] Field of Search ........................ 424/49, 9, 401; 428/402.2, 402.24; 264/4.1, 4.6

[56] References Cited

FOREIGN PATENT DOCUMENTS

| 0 274 961 | 7/1988 | European Pat. Off. . |
|---|---|---|
| 2 551 072 | 3/1985 | France . |
| 2551072 | 3/1985 | France . |
| WO84/00294 | 2/1984 | WIPO . |

*Primary Examiner*—Jyothsan Venkat
*Attorney, Agent, or Firm*—Young & Thompson

[57] ABSTRACT

A nanoparticulate system prepared by: 1) preparing a liquid phase essentially consisting of a solution of cyclodextrin modified by acyl groups in an organic solvent or solvent mixture, an active molecule being optionally added thereto; 2) preparing a second liquid phase essentially consisting of water or an aqueous mixture optionally containing one or more surfactants, and optionally having an active molecule added thereto; and 3) gently stirring one of the liquid phases resulting from 1) or 2) into the other in order to obtain, almost instantaneously, a colloidal solution of modified cyclodextrin nanospheres. If required, all or part of the solvent and all or part of the water may be removed. The system may be used as a carrier for pharmaceuticals, cosmetics, chemicals, etc.

17 Claims, No Drawings

PREPARATION AND USE OF NOVEL CYCLODEXTRIN-BASED DISPERSIBLE COLLOIDAL SYSTEMS IN THE FORM OF NANOSPHERES

This application is a 371 of PCT/FR93/00594, filed on Jun. 16, 1993.

FIELD OF THE INVENTION

The present invention relates to the preparation and the application of a novel cyclodextrin-based dispersible colloidal system in the form of spherical particles of matrix type and of size ranging from 90 to 900 nm (nanospheres), which may contain an active molecule.

BACKGROUND OF THE INVENTION

FR 2 551 072 describes micrometric capsules as a sustained-release pharmaceutical form, which are prepared from polyol esters. These microparticles are not suited to intravascular administration without entailing risks of embolization.

Submicron particles are already known, especially from BE-A-808 034, BE-A-839 748, BE-A-869 107, FR-A-2 504 408, EP-A-02 75 796 and EP-A-03 49 428.

Thus, Belgian Patents No. 808 034 and 839 748 describe submicron particles formed from polymerizable materials such as acrylic or methacrylic acid derivatives, for example methyl or butyl methacrylate, methacrylamide or a mixture of these compounds. The submicron particles formed by micellar polymerization of these various monomers have both the property of totally or partially coating the biologically active substance and the property of forming aqueous colloidal suspensions, which enable these particles thus charged with biologically active molecules to be administered parenterally.

However, the polymers of acrylic or methacrylic acid derivatives described in these patents for the preparation of submicron particles, containing a biologically active molecule, are substantially stable, such that they remain as they are for a long time in the tissues or in the cavity into which they have been administered, and this constitutes a drawback, more particularly in the case of parenteral administration in human medicine.

Belgian Patent No. 869 107 overcomes this back by describing biodegradable nanoparticles containing a biologically active molecule. The material used consists of alkyl cyanoacrylate polymers which have already been used in surgery as tissue adhesives and which are known for their biodegradability.

The major drawback thereof pertains to the structure of the particles obtained, to the toxicity of the degradation products and to the mode of incorporation of the active substance. The procedure described only makes it possible to prepare particles formed of a very dense polymer lattice. The active molecule can only be incorporated by adsorption and the proportion bound is still relatively low. Furthermore, it is difficult to control the molecular weight of the polymer constituting the nanoparticles and it is necessary, especially for the purpose of biological use, to remove the residual monomers and oligomers, the excess polymerization reactants if required (initiator and catalyst) and the surfactants if they are used at high concentration or if they are not biocompatible. However, the purification (ultracentrifugation, dialysis) often proves laborious since filtration of the nanoparticles, in view of their size, is not always possible.

Protein-based nanoparticles have also been proposed, especially by hot denaturation of a water-in-oil emulsion of a solution of a protein such as albumin, (Kramer, P. A.: J. Phar. Sci., 63 1646, 1974) or by desolvation of a solution of a protein, such as gelatin, by an inorganic salt or ethanol (Marty et al., Austr. J. Pharm. Sci., 6, 65, 1978, or Pharm. Acta Helv. 1, 53, 1978), followed, in both cases, by curing using an aldehyde. The Kramer nanoparticles have the main drawback of requiring a pre-emulsification of the aqueous solution of the macromolecular starting material in a continuous oily phase. Since this emulsion needs to be very fine, the ad hoc use of surfactants and of apparatus (sonicator, etc.) is essential in order to obtain nanoparticles of suitable size. As regards the Marty nanoparticles, they make use of considerable quantities of inorganic salts which have to be removed, as do the excess aldehyde and sulphite or metabisulphite used to neutralize the latter.

EP-A-02 75 796 and -03 49 428 describe processes for obtaining nanoparticles of a substance by a desolvation method consisting in mixing two phases of solvents, one being a non-solvent for the substance but soluble in the other solvent.

The nanoparticles according to EP-A-03 49 428 are prepared under certain conditions, that is to say, the temperature of the solvent must be below the coagulation temperature of the protein and the pH of the non-solvent must be distant from the isoelectric point of the protein.

According to the present invention, modified cyclodextrins prepared by acylation of natural cyclodextrins are proposed as base material for the nanospheres. They have the advantage of being biodegradable, their administration is followed by release of the active molecule, and it is possible to obtain biodegradability, which is suitably controlled by making use of modified cyclodextrins which differ from each other in the nature of the alkyl chain of the acyl group used. Such modified cyclodextrins and the preparation thereof are described especially by Ping Zhang, Chang-Chung Ling, A. W. Coleman, Parrot-Lopez and H. Galons in Tetr. Lett. 32, No. 24, 2769-70, 1991.

SUMMARY OF THE INVENTION

Thus, the subject of the invention is a process for the preparation of a cyclodextrin-based dispersible colloidal system in the form of nanospheres, characterized in that:

1) a liquid phase is prepared, consisting of a solution of cyclodextrin modified by acyl groups in an organic solvent or mixture of organic solvents which may or may not contain a surfactant and to which an active molecule may be added, 2) a second liquid phase is prepared, consisting of water or an aqueous mixture, which may or may not contain a surfactant and to which an active molecule may be added, and 3) one of the liquid phases obtained in (1) or (2) is added to the other, with moderate stirring, so as to virtually instantaneously to obtain a colloidal suspension of modified-cyclodextrin nanospheres containing, if required, the said active molecule.

If so desired, all or some of the solvent or of the mixture of solvents and all or some of the water or of the aqueous mixture may be removed so as to obtain a colloidal suspension with the desired concentration of nanospheres or a nanosphere powder.

The modified cyclodextrin used according to the invention is especially a cyclodextrin in which the hydroxyl groups, preferably the secondary hydroxyl groups of each glucose unit forming it, have been esterified with an aliphatic or aromatic acyl group which may be substituted with one or more functional groups, such as a beta-cyclodextrin acylated with an alkanoyl group of 2 to 20 carbon atoms, especially of 6 to 14 carbon atoms. These products are described by Ping Zhang et al. as cited above.

The active molecule is preferably added to the phase in which it is soluble, especially to phase (1) if it is lipid-soluble or to phase (2) if it is water-soluble.

The active molecule may be a medicinal principle, a biological reagent, a cosmetic principle or a chemical product. The invention makes it possible to obtain modified-cyclodextrin nanospheres alone (used as they are) or comprising this active molecule (trapped within its structure).

The organic solvent in phase (1) may be an alcohol such as methanol, ethanol, isopropanol and the like, or a ketone such as acetone.

Water or an aqueous mixture (salt water, acidified water, basified water, and the like) is the non-solvent in phase (2).

The process may be performed at various temperatures (which have little influence on the progress thereof), especially between 0° C. and the boiling temperature of the solvents. The phase (1)/phase (2) volume ratio may preferably range from 0.1 to 1.

The surfactant(s) is (are) especially present in a proportion of from 0.1 to 10%, preferably from 0.2 to by weight of the colloidal suspension obtained in step 3.

Moderate stirring is understood to mean stirring which is sufficient to homogenize the mixture of the phases (1) and (2), for example using a magnetic bar at 50–500 rev/min, for example at 100 rev/min. It is not essential for small amounts of product.

Finally, the colloidal suspension of nanospheres may be concentrated, sterilized, buffered (for example to physiological pH) and freeze-dried at will. For the spheres obtained according to the present invention, the preparation has the advantage of being reversible: it is possible to dissolve the nanospheres and to reprepare the nanospheres from this solution according to the procedure. Furthermore, the nanosphere suspensions exhibit great stability over time.

Under a transmission electron microscope and after negative staining with phosphotungstic acid, the nanospheres obtained according to the invention are in the form of substantially spherical non-contrasted particles and, after very-low-temperature fracture, are in the form of dense spherical particles of matrix type.

Depending on the operating conditions, it is possible to obtain nanospheres the diameter of which ranges from approximately 90 to approximately 900 nanometers, preferably from 90 to 300 nm, especially 150 to 300 nm.

The nanospheres obtained by the invention may contain an active molecule within their lattice, for example a medicinal molecule for human or veterinary use or a diagnostic product. As medicinal molecule, there may be mentioned more particularly chemical products endowed with pharmacological properties and, for example, antimitotic or antineoplastic substances such as methotrexate, actinomycin D, adriamycin, daunorubicin, bleomycin and vincristine or antibiotic substances such as penicillins, cephalosporins and nalidixic acid, aminoglycoside-type antibiotics and those of the virginiamycin family and hormonal substances, especially steroidal hormones. These medicinal molecules may especially be high-molecular-weight chemical compounds such as insulin and heparin and the term "medicinal molecule" also comprises biological products such as antigens, enzymes, proteins, viruses or vital, bacterial or cell constituents. The nanospheres according to the invention may also contain a diagnostic product such as, for example, fluorescein and radioactive human seralbumin.

In human or veterinary medicine, the nanospheres of the invention may be used as vectors for medicaments administered orally, subcutaneously, intradermally, intramuscularly or intravenously with or without a suitable excipient and their diffusion into tissues makes them particularly advantageous for systemic treatments.

In contrast with the nanoparticles formed of a dense lattice, the nanospheres of the present invention have the advantage of allowing a markedly higher level of incorporation. This is due to the possibility of double loading, firstly a loading in the lattice and secondly a loading in the cavity of the cyclodextrin, on condition that the molecule introduced has a suitable conformation relative to the cavity.

DETAILED DESCRIPTION OF THE INVENTION

The invention is illustrated by the following examples:

EXAMPLE 1

Preparation of 6-carbon-modified cyclodextrin nanospheres

A beta-cyclodextrin is used in which the secondary OHs of the glucose units forming it have been esterified with hexanoyl groups, prepared according to Ping Zhang et al.

| Phase 1 | |
|---|---|
| 6-C-modified beta-cyclodextrin | 50 mg |
| acetone | 50 ml |
| Phase 2 | |
| Pluronic (R) F68 | 62.5 mg |
| demineralized or distilled water | 25 ml |

Phase 1 is added to phase 2 with magnetic stirring. The medium immediately becomes opalescent by formation of modified-cyclodextrin nanospheres. The average size of the nanospheres, measured by a laser-beam diffractometer (Nanosizer (R) from Coultronics), is 180 nm with an average dispersion index of 0.08.

The suspension may be concentrated under reduced pressure to the desired volume, for example 5 ml or thereabouts.

The appearance of the nanosphere suspension remains unchanged after standing for a prolonged period (14 months) and there is no sign, in particular, either of irreversible sedimentation or of variation in the size of the nanospheres.

EXAMPLE 2

(Variant of Example 1)

The process is performed as in Example 1, but by adding the aqueous phase to the acetone phase. The nanospheres obtained have the same characteristics as in Example 1.

EXAMPLE 3

(Variant of Example 1)

The process is performed as in Example 1, but by adding the acetone phase to the aqueous phase without stirring the medium. The nanospheres obtained are 200 nm in size and have an average dispersion index of 0.5.

EXAMPLE 4

(Variant of Example 1)

The process is performed as in Example 1, but without addition of surface agent to the aqueous phase. The nanospheres obtained are 200 nm in size and have an average dispersion index of 0.6.

EXAMPLE 5

Sterile preparation of 6-carbon-modified cyclodextrin nanospheres

The process is performed as in Example 1, and the suspension is then sterilized in an autoclave at 120° C. for 15 minutes. The average particle size remains virtually unchanged after sterilization.

EXAMPLE 6

Freeze-drying preparation of 6-carbon-modified cyclodextrin nanospheres

The process is performed as in Example 1, and the suspension is then freeze-dried. The addition of a cryoprotector (maltose, trehalose and the like) is not essential. The average particle size measured immediately after freeze-drying remains unchanged.

EXAMPLE 7

Preparation of 12-carbon-modified cyclodextrin nanospheres

The process is performed as in Example 1, replacing 6-carbon-modified cyclodextrin by 12-carbon-modified cyclodextrin, that is to say a beta-cyclodextrin acylated with dodecanoyl groups. The average size of the nanospheres is 172 nm with an average dispersion index of 0.1.

These nanospheres may be sterilized in the autoclave and freeze-dried as for those with 6 carbon.

EXAMPLE 8

Preparation of 14-carbon-modified cyclodextrin nanospheres

The process is performed as in Example 1, replacing 6-carbon-modified cyclodextrin by 14-carbon-modified cyclodextrin, that is to say one acylated with tetradecanoyl groups. The average size of the nanospheres is 110 nm with an average dispersion index of 0.1. The 14-carbon-modified cyclodextrin nanospheres may be sterilized in the autoclave and freeze-dried as for those with 6 carbon.

EXAMPLE 9

Stability of the cyclodextrin nanospheres in the presence of variable ionic strengths The process is performed as indicated in Example 1. After concentration of the suspension of modified-cyclodextrin nanospheres to a volume of 10 ml, increasing quantities of sodium chloride are progressively added thereto. The nanosphere suspension is perfectly stable when the sodium chloride concentration corresponds to. isotonicity with blood and remains so up to a concentration which is 3 times greater than the isotonic concentration.

EXAMPLE 10

Stability of the cyclodextrin nanospheres in the presence of an acidic or basic medium The process is performed as indicated in Example 1. After concentration of the suspension of cyclodextrin nanospheres to a volume of 10 ml, increasing quantities of hydrochloric acid (1N) or of sodium hydroxide (1N) are progressively added thereto. The nanosphere suspension is perfectly stable.

EXAMPLE 11

Temperature-stability of the cyclodextrin nanospheres

The process is performed as indicated in Example 1. After concentration of the suspension of cyclodextrin nanospheres to a volume of 10 ml, each batch is placed at 4° C., 25° C. and 40° C.

The suspensions remain stable over time and do not exhibit, after storage for 14 months, either irreversible sedimentation or variation in the size of the nanospheres.

EXAMPLE 12

Preparation of nanospheres in the presence of a salt

The process is performed as indicated in Example 1, but 90 mg of sodium chloride are added to the aqueous phase. After concentration of the suspension of nanoparticles to a volume of 10 ml, which corresponds, taking the sodium chloride into account, to isotonicity with blood, the nanospheres have an average size of 200 nm with an average dispersion index of 1.

The suspension remains stable over time and does not exhibit, after storage for 14 months, either irreversible sedimentation or variation in the size of the nanoparticles.

EXAMPLE 13

Addition of non-solvent to the solvent phase

The process is performed as in Example 1, but the cyclodextrin is dissolved in an acetone/water mixture (90/10, v/v) instead of pure acetone. The presence of a low proportion of non-solvent for the cyclodextrin in a solvent gives nanospheres the average size of which is 180 nm with an average dispersion index of 0.5.

EXAMPLE 14

Stability of the cyclodextrin nanospheres to ultrasound

The process is performed as in Example 1. After concentration of the suspension of cyclodextrin nanospheres to a volume of 10 ml, the suspension of cyclodextrin nanospheres is placed in an ultrasound bath for 3 hours.

The suspension remains stable over time and does not exhibit, after storage for 14 months, either irreversible sedimentation or variation in the size of the nanospheres.

EXAMPLE 15

Preparation of nanospheres in the presence of a lipophilic active principle

The process is performed as in Example 1, but 20 mg of indomethacin are added to the acetone phase. The nanospheres obtained have an average size of 200 nm with a dispersion index of 0.5. After ultracentrifugation and assay of the indomethacin in the dispersing phase, the quantity of active principle incorporated into the nanospheres represents 70% of the initial quantity.

EXAMPLE 16

Preparation of nanospheres containing doxorubicin

The process is performed as in Example 1, but 5 mg of doxorubicin are added to the aqueous phase. The nanospheres obtained have an average size of 200 nm and an average dispersion index of 1. After ultracentrifugation and assay of the doxorubicin in the dispersing phase, the quantity of active principle incorporated into the nanospheres represents 60% of the initial quantity.

EXAMPLE 17

Preparation of nanospheres containing progesterone

The process is performed as in Example 1, but 150 mg of progesterone are added to phase 1. The nanospheres obtained have an average size of 120 nm and a dispersion index of 0.2. After ultracentrifugation and assay of the progesterone in the dispersing phase, the quantity of active principle incorporated into the nanospheres represents 60% of the initial quantity.

EXAMPLE 18

Preparation of nanospheres containing amphotericin B

The process is performed as in Example 1, but 6 mg of amphotericin B are added to phase 1. The nanospheres obtained have an average size of 180 nm and a dispersion index of 0.2. After ultracentrifugation and assay of the amphotericin in the dispersing phase, the quantity of active principle incorporated into the nanospheres represents 90% of the initial quantity.

EXAMPLE 19

Preparation of nanospheres containing a lipophilic dye, Sudan III

The process is performed as in Example 1, but 5 mg of Sudan III are added to phase 1. A small amount precipitates and remains on the filter. The nanospheres obtained have an average size of 130 nm and a dispersion index of 0.2.

The nanospheres obtained according to the invention may find applications in many technical fields.

As active principle "vectors" in human and animal therapy, the nanospheres make it possible to envisage:

- reaching new sites of action, in particular intracellular sites or even intralysosomal sites;
- using new routes of administration for the known active principles, enhancing the stability and/or the absorption of the active principles or making it possible to produce intravascularly injectable forms of insoluble active principles;
- modifying the distribution of the active principles in the tissues, by better targetting towards favourable sites of action and/or by diversion away from sites of undesirable or even toxic effects (enhancement of the therapeutic index).

In pharmacy, these colloidal dispersions of cyclodextrin may make it possible especially:

to prepare injectable forms of insoluble medicaments, to stabilize a medicinal active principle.

In the field of phytopharmacy, the nanospheres may convey insecticides, pesticides, etc. Their size can make it possible to envisage a more powerful action by better penetration across the cuticle. The low viscosity of the dispersion allows for very easy spraying in the form of very small-sized droplets, which are more effective because they provide fuller coverage.

In cosmetology, the cyclodextrin nanospheres may transport anti-radical products or the like into the skin.

In the field of paints, varnishes and surface treatments in general, the nanospheres make it possible to convey pigments, reactants and stripping agents in the form of an aqueous dispersion of very low viscosity, which is easy to spray or to apply and which can, if necessary, be made viscous or even adhesive (resuspending of the nanospheres in a suitable vehicle). The reduced size of the nanospheres leads to a very high fineness of the deposit and to very high homogeneity, for example of pigmentation.

The nanospheres obtained according to the invention may be used in the fields of printing and of reprographics, in the field of surface treatment of textiles and fibres or others, in the field of photography, in the field of lubrication or in the agricultural field.

We claim:

1. Process for the preparation of a cyclodextrin-based dispersible colloidal system in the form of nanospheres, which comprises:

(a) preparing a liquid phase consisting essentially of a solution of cyclodextrin modified by $C_2$–$C_{20}$ alkanoyl groups in an organic solvent selected from the group consisting of methanol, ethanol, isopropanol, acetone, and a mixture thereof;

(b) preparing a second liquid phase consisting essentially of water or an aqueous mixture; and (c) adding one of the liquid phases obtained in step (a) or step (b) to the other, with moderate stirring, so as virtually instantaneously to obtain a colloidal suspension of modified-cyclodextrin nanospheres.

2. Process according to claim 1, wherein the modified cyclodextrin is a β-cyclodextrin acylated with an aliphatic or aromatic acyl group.

3. Process according to claim 1, wherein the modified cyclodextrin is a β-cyclodextrin esterified with alkanoyl groups of 2 to 20 carbon atoms.

4. Process according to claim 3, wherein the modified cyclodextrin is a β-cyclodextrin esterified with alkanoyl groups of 6 to 14 carbon atoms.

5. Process according to claim 1, further comprising the step of adding an active molecule to at least one of said liquid phases prepared in step a) and b), whereby upon performing step (c) the active molecule is contained within the modified-cyclodextrin nanospheres.

6. Process according to claim 5, wherein the active molecule is selected from the group consisting of a medicinal active principle, a medicinal precursor for mammal use, a biological reagent, a cosmetic principle, a virus, a viral, bacterial or cell constituent, an antigen, an allergen, and an enzyme.

7. Process according to claim 1, wherein the volume ratio of the first liquid phase to the second liquid phase is from 0.1 to 1.

8. Process according to claim 1, further comprising removing all the organic solvent, and removing all of the water or aqueous mixture thereby obtaining a nanosphere powder.

9. Process according to claim 8, wherein all of the water is removed by freeze-drying.

10. Process according to claim 1, further comprising adjusting the concentration of the colloidal suspension obtained in step (c) by removing a part of the organic solvent, and by removing a part of the water or aqueous mixture.

11. Process according to claim 1, wherein at least one of said liquid phases comprises a surfactant.

12. Process according to claim 11, wherein the surfactant is present in a proportion of from 0.1 to 10% by weight of the colloidal suspension obtained in step (c).

13. Process according to claim 12, wherein the surfactant is present in a proportion of from 0.2 to 2% by weight of the colloidal suspension.

14. Process according to claim 5, wherein the active molecule is selected from the group consisting of antimimotic or antineoplastic substances, antibiotic substances, steroidal hormones, fluorescein, radioactive human seralbumin and dies.

15. Process according to claim 5, wherein the active molecule is selected from the group consisting of methotrexate, actinomycin D, adriamycin, daunorubicin, bleomycin, vincristine, penicillins, cephalosporins, nalidixic acid, aminoglycoside antibiotics, virginiamycin antibiotics, fluorescein, radioactive human seralbumin, indomethacin, doxorubicin, progesterone, amphotericin B.

16. Process according to claim 1, wherein the solution of modified-cyclodextrin of step (a) or the aqueous mixture of step (b) or both include a nonionic surfactant having the following structure:

$$HO(CH_2CH_2O)_{75}(CH(CH_3)CH_2OH)_{30}(CH_2CH_2)_{75}H.$$

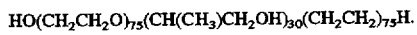

17. Process for the preparation of a cyclodextrin-based dispersible colloidal system in the form of nanospheres, which comprises:

(a) preparing a liquid phase consisting essentially of a solution of beta-cyclodextrin modified by $C_2$–$C_{20}$ alkanoyl groups in an organic solvent selected from the group consisting of methanol, ethanol, isopropanol, acetone, and a mixture thereof;

(b) preparing a second liquid phase consisting essentially of water or an aqueous mixture; and (c) adding one of the liquid phases obtained in step (a) or step (b) to the other, with moderate stirring, so as virtually instantaneously to obtain a colloidal suspension of modified-beta-cyclodextrin nanospheres.

* * * * *